(12) United States Patent
Kanayama

(10) Patent No.: US 9,046,504 B2
(45) Date of Patent: Jun. 2, 2015

(54) AUTOMATIC ANALYSIS APPARATUS

(75) Inventor: Shoichi Kanayama, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/403,183

(22) Filed: Feb. 23, 2012

(65) Prior Publication Data

US 2012/0216610 A1  Aug. 30, 2012

(30) Foreign Application Priority Data

Feb. 24, 2011  (JP) ................................ P2011-038700

(51) Int. Cl.
  *G01N 1/22*  (2006.01)
  *G01N 35/02*  (2006.01)
  G01N 35/04  (2006.01)
  G01N 35/10  (2006.01)
(52) U.S. Cl.
  CPC .............. *G01N 35/025* (2013.01); *G01N 35/04* (2013.01); *G01N 35/10* (2013.01); *G01N 35/026* (2013.01); *G01N 35/1011* (2013.01); *G01N 35/109* (2013.01); *G01N 2035/0441* (2013.01)
(58) Field of Classification Search
  CPC ...... G01N 35/026; G01N 35/04; G01N 35/10
  USPC ........................................... 73/290 R, 863.01
  See application file for complete search history.

(56) References Cited

U.S. PATENT DOCUMENTS

| 2009/0133511 | A1* | 5/2009 | Heinze et al. | 73/863.01 |
| 2009/0223308 | A1* | 9/2009 | Fukuma | 73/863.01 |
| 2010/0300217 | A1* | 12/2010 | Mizumoto | 73/863.01 |
| 2011/0244583 | A1* | 10/2011 | Tatsutani et al. | 436/55 |

FOREIGN PATENT DOCUMENTS

| JP | 8-35970 | 2/1996 |
| JP | 11-258248 | 9/1999 |
| JP | 3029330 | 2/2000 |

* cited by examiner

*Primary Examiner* — Hezron E Williams
*Assistant Examiner* — David Z Huang
(74) *Attorney, Agent, or Firm* — Oblon, McClelland, Maier & Neustadt, L.L.P.

(57) ABSTRACT

An automatic analysis apparatus that can suction a target sample through an sample dispensing probe at a single sample dispensing position by transferring a sample rack holder having one or more sample containers from a first sampler unit to a second sampler unit and by moving the transferred sample rack in a horizontal direction and up-and-down directions at the fixed single sample dispensing position. By fixing a fluid sampling position of a sample container held by a sample rack at the single position, a sample dispensing accuracy of an automatic analysis apparatus can be increased.

12 Claims, 7 Drawing Sheets

AUTOMATIC ANALYSIS APPARATUS

CROSS-REFERENCE TO RELATED APPLICATIONS

This application claims priority from and the benefit of Japanese Patent Application No. 2011-38700 filed on Feb. 24, 2011, the contents of which are expressly incorporated herein by reference in their entirety.

BACKGROUND OF THE INVENTION

A. Field of the Invention

The present embodiments relate to an automatic analysis apparatus for analyzing items contained in an object sample fluid obtained from an object.

B. Background

An automatic analysis apparatus optically measures changes of color tones or turbidity changes that are generated due to reactions between a target object sample and reagents corresponding to each of analyzing items. The automatic analysis apparatus generates analysis data representing a density or an enzyme activity of each analyzing item in the target object sample.

An automatic analysis apparatus includes a sampler unit and a sample dispensing probe. The sampler unit movably holds a plurality of sample containers, each containing a sample, such as a general sample, an accuracy control sample or an object sample corresponding to each of analyzing items. The sample dispensing probe suctions a sample contained in a sample container and ejects the suctioned sample into a reaction cuvette for reacting with a reagent.

There are two types of sampler units for an automatic analysis apparatus. One is a rack type sampler (hereinafter simply says as a "rack sampler") and the other is a disk type sampler (hereinafter simply says as a "disk sampler"). A rack sampler moves in parallel a plurality of racks; each rack holds a plurality of sample containers. A disk sampler rotatably holds a plurality of sample racks.

A disk sampler can repeatedly stop an object sample at a suctioning position for suctioning the sample contained in a sample container through a sample dispensing probe. Accordingly, standard sample containers containing "standard" samples that are used for repeatedly performing calibration measurements at a regular interval and "control" samples for controlling data accuracy are usually mounted on the disk sampler, together with sample containers containing general patient samples (hereinafter, "general" samples). In contrast to this, since a rack sampler has a large capacity for holding many object sample racks and can perform an interrupt measuring process during general measurements, general samples that need not to be repeatedly measured in a regular interval are mounted on the rack sampler.

As just described, a rack sampler can mount many samples and can perform an interrupt processing during a measurement. However, it is difficult for the rack sampler to perform calibration measurements and control measurements. On the other hand, while a disk sampler can easily perform calibration measurements and control measurements, it is difficult to perform interrupting measurements for an urgent patient sample (hereinafter "urgent" sample) during the general measurements. Further, a disk sampler has a reduction problem of measurement accuracy since the disk sampler easily happens to generate differences of sampling performances due to variations of sampling positions.

SUMMARY OF THE INVENTION

The present embodiments solves the above-mentioned problems and defects of a rack sampler and a disk sampler and provides an automatic analysis apparatus that can increase sample dispensing accuracy. Thus, the automatic analysis apparatus consistent with the embodiments can suction a target sample through a sample dispensing probe by fixing a fluid sampling position of a sample container held by a sample rack at a single position. Namely, a sample rack holding one or more sample containers is transferred from a first sampler unit to a second sampler unit. The transferred sample rack is moved in a horizontal direction for placing at a fixed sampling position. Further, the transferred sample rack is moved in up-and-down directions at the fixed sampling position for suctioning at a single sample dispensing position.

To achieve the above-mentioned effects, an automatic analysis apparatus consistent with one embodiment includes: a first sampler unit configured to movably mount a plurality of sample racks, each holding a plurality of sample containers; a first moving device provided in the first sampler unit so as to transfer a target sample rack holding a target sample container to an outside of the first sampler unit; a first container reader configured to read each identification data of a plurality sample containers held by the target sample rack transferred through the first moving device; a second sampler unit configured to movably mount the target sample rack transferred through the first moving device; a second moving device provided in the second sampler unit so as to move each of the plurality of sample containers held by the transferred target sample rack to a single sample dispensing position; a second container reader configured to read each identification data of the plurality of sample containers held on the target sample rack moved by the second moving device; and a sample dispensing probe configured to suction the target sample contained in a target sample container identified by the second container reader at the single sample dispensing position.

To achieve the above-mentioned effects, an automatic analysis apparatus consistent with another embodiment includes: a first sampler unit configured to movably mount a plurality of sample racks, each holding a plurality of sample containers; a first moving device configured to transfer a target sample rack among the plurality of sample racks to an outside of the first sampler unit; a first container reader configured to read each identification data of a plurality of sample containers held on the target sample rack transferred by the first sampler unit; a second sampler unit configured to movably mount a plurality of another sample racks different from the plurality of sample racks mount on the first sampler unit; a second moving device configured to transfer each of the plurality of another sample racks mounted on the second sampler unit to an outside of the second sampler unit; a second container reader configured to read each identification data of a plurality of sample containers held on the sample rack transferred outside of the second sampler unit by the second moving device; a third moving device configured to move each sample container held on the plurality of sample racks moved by the first moving device and the plurality of another sample racks moved by the second moving device to a single sample dispensing position; and a sample dispensing probe configured to suction each sample contained in each of the transferred sample containers mounted on the target sample racks at the single sample dispensing position.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings.

DESCRIPTION OF THE EMBODIMENTS

Figure 1:
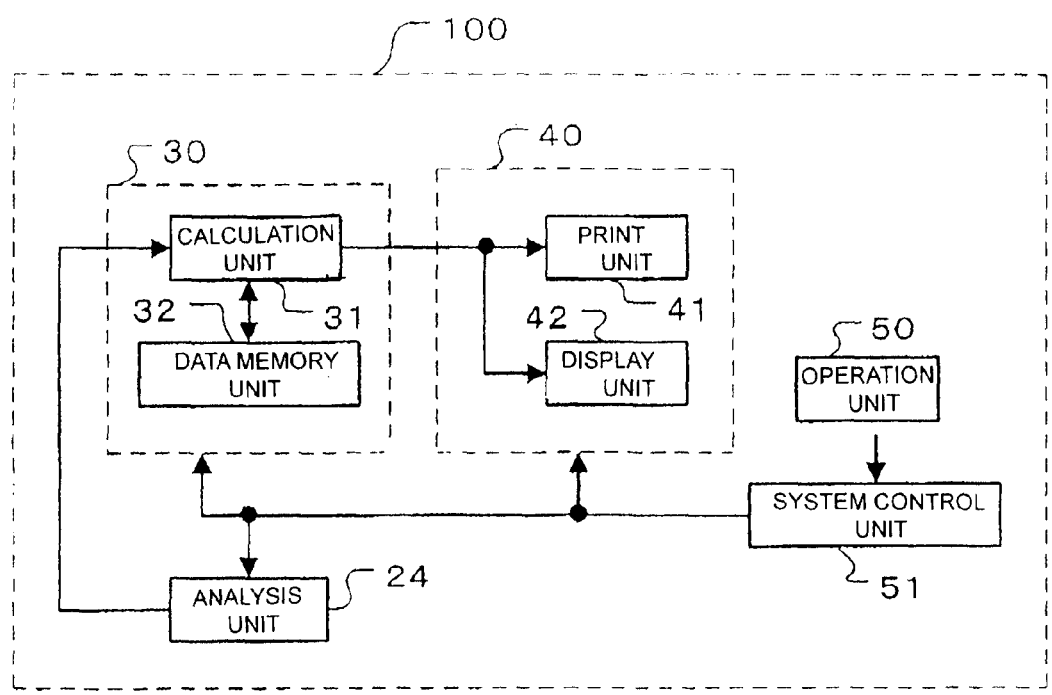
FIG. 1 is a block diagram illustrating a construction of an automatic analysis apparatus consistent with the embodiment.

As illustrated in FIG. 1, the automatic analysis apparatus 100 includes an analysis unit 24 and a data processing unit 30. The analysis unit 24 measures a mixed solution of each sample of a general sample, control sample and an object sample with a corresponding reagent. The data processing unit 30 generates calibration data, control data and analysis data based on general data, control data and object data measured by the analysis unit 24.

The automatic analysis apparatus 100 further includes an output unit 40, an operation unit 50 and a system control unit 51. The output unit 40 outputs calibration data, control data and analysis data generated by the data processing unit 30. The operation unit 50 inputs analysis parameters for each of analyzing items and various command signals. The system control unit 51 totally controls the analysis unit 24, the data processing unit 30 and the output unit 40.

Figure 2:
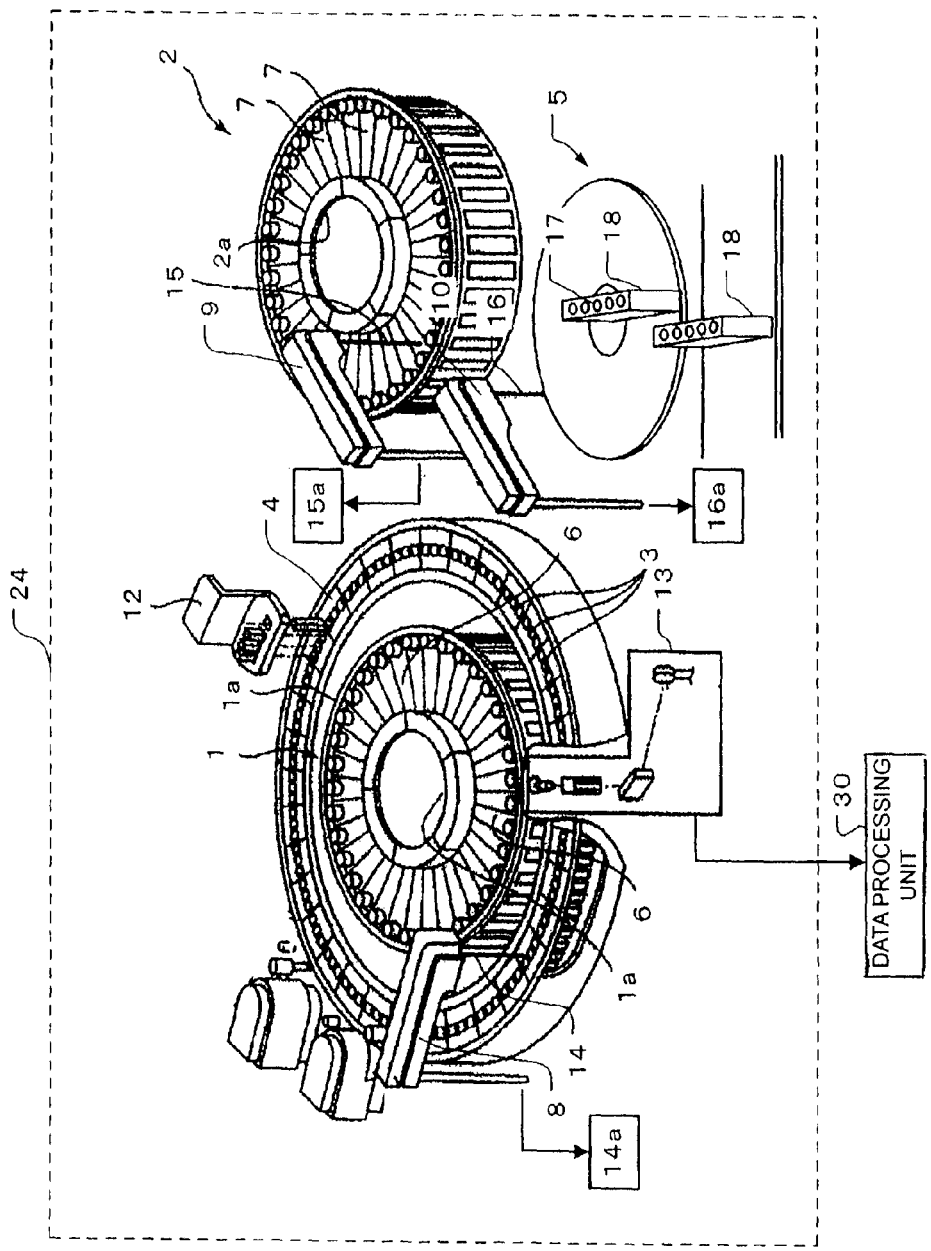
FIG. 2 is a schematic block diagram of an embodiment of the analysis unit in the automatic analysis apparatus shown in FIG. 1.

As illustrated in FIG. 2, the analysis unit 24 includes a reaction disk 4 and a sampler unit 5. The reaction disk 4 rotatably holds a plurality of reaction cuvettes 3 disposed on the circumference of a circle. The sampler unit 5 movably supports a plurality of sample racks 18, each holding a plurality of sample containers 17 for containing respective samples.

The analysis unit 24 further includes a first reagent rack 1, a second reagent rack 2 and a plurality of reagent containers 6. Each of the reagent containers 6 contains a first reagent of one-reagent system or a two-reagent system used for each of analyzing items. The first reagent rack 1 rotatably holds a reagent warehouse 1a for storing the plurality of reagent containers 6. The second reagent rack 2 rotatably holds a plurality of reagent containers 7 for storing a second reagent as a pair of the first reagent in the two reagent system, and a reagent warehouse 2a for storing the plurality of reagent containers 7.

The analysis unit 24 includes a sample dispensing probe 16, a sample sensor 16a and a sample dispensing arm 10. The sample dispensing probe 16 suctions a sample in a sample container 17 held by a sample rack 18 in the sampler unit 5 and ejects the dispensed sample into a reaction cuvette 3. The sample sensor 16a detects the sample in the sample container 17 by a touch of a bottom head portion of the sample dispensing probe 16 with a fluid level the sample. The sample dispensing arm 10 rotatably holds the sample dispensing probe 16. The sample dispensing arm 10 further moves the sample dispensing probe 16 upward and downward.

The analysis unit 24 further includes a first reagent dispensing probe 14, a first reagent sensor 14a and a first reagent dispensing arm 8. The first reagent dispensing probe 14 dispenses a first reagent into a reaction cuvette 3 by suctioning the first reagent contained in a reagent container 6 held by the reagent rack 1 and ejecting it in the reaction cuvette 3. In the reaction cuvette 3, a sample has been ejected. The first reagent sensor 14a detects the first reagent contained in the reagent container 6 when a lower end portion of the first reagent dispensing probe 14 touches to fluid level of the first reagent fluid level. The first reagent dispensing arm 8 hold the first reagent dispensing probe 14 so as to rotate and move upward and downward.

The analysis unit 24 further includes a second reagent dispensing probe 15, a second reagent sensor 15a and a second reagent dispensing arm 9. The second reagent dispensing probe 15 dispenses a second reagent into the reaction cuvette 3 containing the first reagent by suctioning the second reagent in a reagent container 7 held by the reagent rack 2 and ejecting it in the reaction cuvette 3. The second reagent sensor 15a detects second reagent contained in the reagent container 7 by touching a fluid level of the second reagent and a lower end portion of the second reagent dispensing probe 15. The second reagent dispensing probe 15 is rotated and moved upward and downward by the second reagent dispensing arm 9.

The analysis unit 24 further includes a light measuring unit 13 for measuring a mixed solution of the sample and the first reagent ejected in a reaction cuvette 3 or a mixed solution of the sample and the first and second reagents, and a reaction cuvette cleaning unit 12 for cleaning the reaction cuvette 3 after measurement of the mixed solution.

The light measuring unit 13 includes a light source and detection elements for detecting a light emitted from the light source. The light measuring unit 13 irradiates a light to a rotatably moving reaction cuvette 3 on a reaction disk 4 and detects light transmitted through the mixed solution. The light measuring unit 13 generates general sample data based on detection signals transmitted through a mixed solution containing a general sample. The light measuring unit 13 also generates control sample data based on detection signals transmitted through a mixed solution containing control sample. Further the light measuring unit 13 generates object sample data based on detection signals transmitted through a mixed solution containing an object sample. Each of these general sample data, control sample data and object sample data is output to the data processing unit 30.

The data processing unit 30 shown in FIG. 1 includes a calculation unit 31 and a data memory unit 32. The calculation unit 31 processes each of these general sample data, control sample data and object sample data generated by the light measuring unit 13 (FIG. 2) and generates calibration data, control data and analysis data, respectively. The data memory unit 32 stores each of calibration data, control data and analysis data generated in the calculation unit 31.

The calculation unit 31 generates calibration data representing a relationship between the general value and a general data to each of analyzing items based on the general sample data outputted from the light measuring unit 13 and a predetermined general value set of the general sample data and outputs the generated calibration data to the output unit 40. The calibration data is stored in the data memory unit 32.

Each calibration data of analyzing items corresponding to the control sample data supplied from the light measuring unit 13 is read out from the data memory unit 32. By using the read out calibration data, control data representing density value and activity value are generated from the control sample data. The generated control data is outputted to the output unit 40 and also stored in the data memory unit 32.

Further, each calibration data of analyzing items corresponding to the object sample data outputted from the light measuring unit 13 is read out from the data memory unit 32. By using the calibration data, analysis data representing a density value and an activity value are generated from the object sample data. The generated analysis data is provided to the output unit 40 and also stored in the data memory unit 32.

The data memory unit 32 includes a memory device such as a hard disk and stores each calibration data outputted from the calculation unit 31 with respect to each analyzing items. Also, the data memory unit 32 stores each control data outputted from the calculation unit 31 for each analyzing item. The data memory unit 32 further stores each analysis data outputted from the calculation unit 31 for each analyzing item in relation to each respective object sample.

The output unit 40 includes a print unit 41 for printing out the calibration data, control data and analysis data outputted from the calculation unit 31 in the data processing unit 30, and a display unit 42 for displaying the outputs. The print unit 41 includes a printer for printing out the calibration data, control data and analysis data on a paper in accordance with a predetermined format.

The display unit 42 includes monitors, such as a cathode ray tube (CRT) or a liquid crystal panel for representing calibration data, control data and analysis data. The display unit 42 displays an analysis parameter setting screen for setting analysis parameters for analyzing items by the automatic analysis apparatus 100, for instance, such as a sample amount and a reagent amount to be ejected in a reaction cuvette 3 of the analysis unit 24. The display unit 42 further displays a sample's ID for a measuring object sample and an object sample data setting screen for setting analyzing items of the object sample.

The operation unit 50 includes input devices, such as a keyboard, a mouse, buttons and a touch key panel for setting, for example, analysis parameters for each of analyzing items. And the operation unit 50 performs input operation for setting sample's ID and analyzing items. Further, the operation unit 50 inputs a time interval for measuring the control sample.

The system control unit 51 includes a central processing unit (CPU) and a memory circuit. After storing input data, such as analysis parameters for each of analyzing items in the memory circuit, the CPU in the system control unit 51 controls entire operations of the analysis unit 24, the data processing unit 30 and the output unit 40 based on the inputted data.

Figure 3:
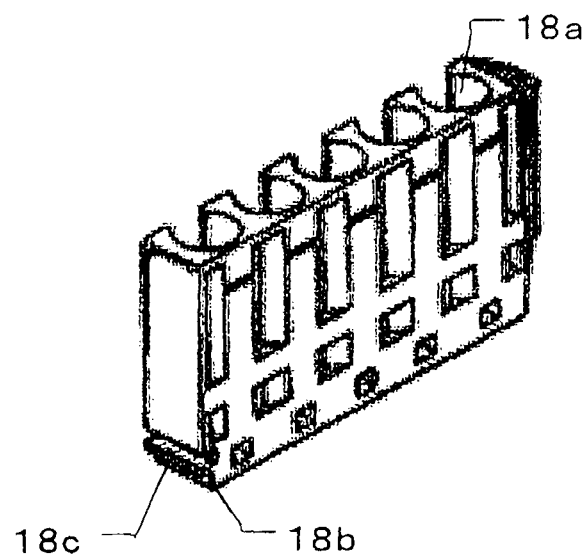
FIG. 3 is a perspective view of the sample rack moved in the analysis unit in the automatic analysis apparatus shown in FIG. 1.

As illustrated in FIG. 3, the sample rack 18 includes a plurality of opening sections 18a arranged in a longitudinal direction, a hollow 18b formed adjacent a tip portion of a bottom surface and an IC chip 18c provided adjacent the hollow 18b. For instance, five opening sections 18a are arranged in a longitudinal direction in FIG. 3. The opening sections 18a hold sample containers 17, such as blood collection tubes, on a line. The hollow 18b is used for moving the sample rack 18 to the sampler unit 5. In the IC chip 18c, an identification data (rack's ID) for each particular sample rack 18 is rewritable written. In accordance with the rack's ID, a particular sample rack is classified into, such as, a "general", a "control", an "urgent" or "general (non-emergency)".

Figure 4:
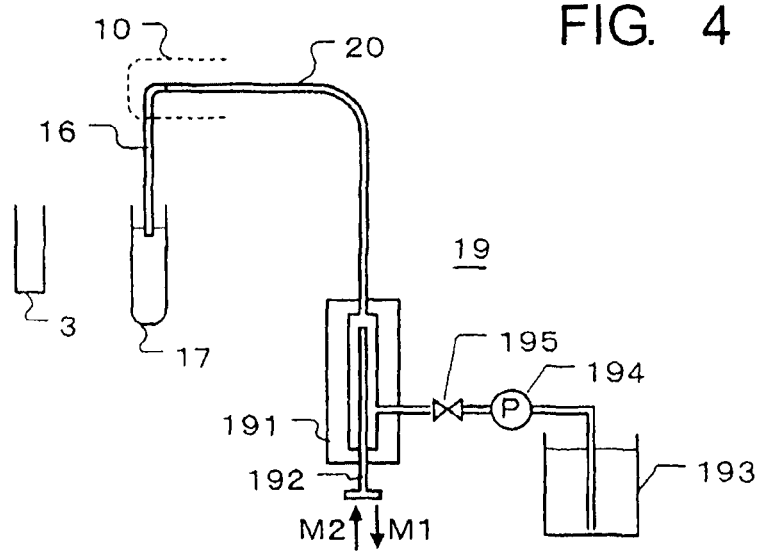
FIG. 4 is a schematic diagram illustrating a sample dispensing construction unit including a sample dispensing probe.

FIG. 4 depict a construction of each unit relating to dispensing of a sample. A sample dispensing probe 16 is made of a hollow cylinder having a top edge opening and a bottom edge opening for suctioning and ejection a sample. The top edge opening of the sample dispensing probe 16 is connected to one edge portion of the flexible tube 20. The dispense probe 16 and the flexible tube 20 are in communication to the syringe 19. To facilitate understanding, hereinafter, the embodiment is explained so that an axis direction of the sample dispensing probe 16 is a vertical direction, and an orthogonal direction to the vertical direction is a horizontal direction.

The syringe 19 includes of a cylinder 191, a plunger 192, a tank 193, a pump 194 and an on-off valve 195. One edge of the cylinder 191 is connected to other edge of the tube 20. And a plunger 192 is inserted into an opening provided at the other edge portion of the cylinder 191. The tank 193 pools a fluid pressure transmission medium, for example a water, for filling in each of the sample dispensing probe 16, the tube 20 and the cylinder 191. The pump 194 supplies the pressure transmission medium retained in the tank 193 to the cylinder 191. The on-off valve 195 turns on and off a fluid path communicating between the cylinder 191 and the pump 194.

In case of suctioning a sample, the sample dispensing probe 16 rotates in a horizontal direction, and stops above a sample container 17 held on the sample rack 18. Then, the sample dispensing probe 16 moves downward and stops when a probe lower end portion touches to a sample surface in the sample container 17. The contact position of the surface probe lower end portion and the sample surface is detected by the sample sensor 16a shown in FIG. 2. Then, suctioning of the sample is begun by moving the plunger 192 in the arrow M1 direction during when the on-off valve 195 closes a flow channel between the cylinder 191 and the pump 194.

In case of ejecting the sample, the sample dispensing probe 16 rotates in the horizontal direction and stops above to the reaction cuvette 3. Then, the sample dispensing probe 16 moves downward and the probe lower end portion stops at an ejecting position in the reaction cuvette. By driving the plunger 192 in an arrow M2 direction, the sample suctioned from the sample container 17 is ejected into the reaction cuvette.

Figure 5:
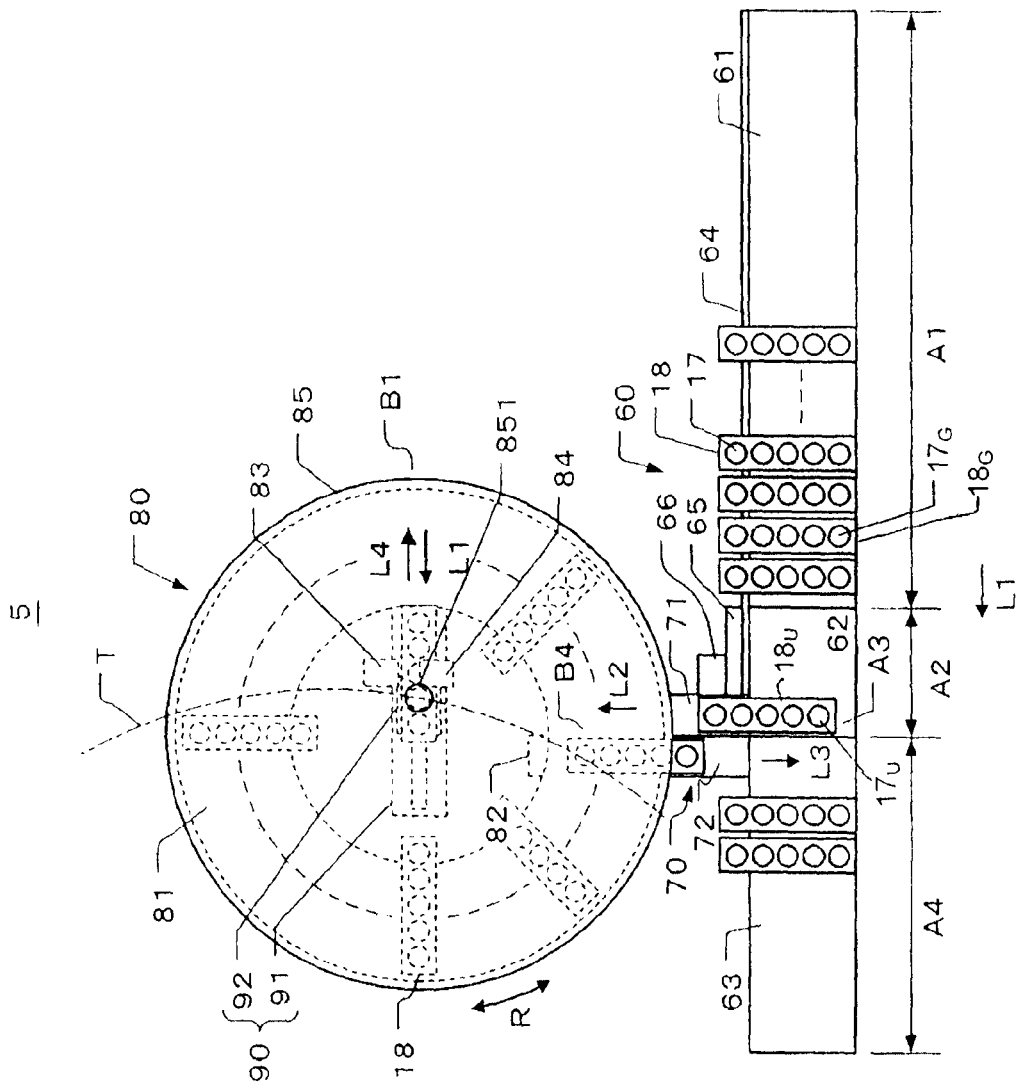
FIG. 5 is a schematic block diagram of an embodiment of the sampler unit in the automatic analysis apparatus shown in FIG. 1.

FIG. 5 illustrates a construction of a first embodiment of the sampler unit 5. FIGS. 6A and 6B show moving directions of the sample rack 18 that is moved to a position at where the sample dispensing probe 16 can suction the sample.

In case of dispensing a sample at a plurality of positions, the sample dispensing probe is moved at each of the plurality of positions. Then, an equal amount of the sample is suctioned at the respective position and the equal amount of the sample is ejected in the reaction cuvette. In accordance with a movement of the sample dispensing probe, the flexible tube 20 also is moved. When the suction position is moved at a different position, a different amount of the sample happens to be contained in the tube due to differences of the tube flexure. For instance, an ejection amount of the sample suctioned at a first position in a reaction cuvette may have a small difference from the ejection amount of the sample suctioned at a second position in the reaction cuvette. As a result, a reduction of dispensing accuracy of the sample of a minute amount occurs. To solve the problem, according to the present embodiment; a suctioning position of the sample by the sample dispensing probe is fixed at a predetermined position. And the sample rack is moved to the fixed predetermined position.

In FIG. 5, the sampler unit 5 includes a first sampler unit 60, a first moving device 70, a second sampler unit 80 and a second moving device 90. The first sampler unit 60 movably holds a plurality of sample racks 18 on a longitudinal direction of a belt, i.e., a moving direction of a rack. The first moving device 70 moves a designated sample rack 18 in an orthogonal direction to the rack moving direction, i.e., bring-in and ejection directions of a rack. The second sampler unit 80 rotatably holds the plurality of sample racks 18. The second moving device 90 moves the sample container 17 in the sample rack 18 moved from the first sampler unit 60 to the second sampler 80 by the first moving device 70 to a position when the sample dispensing probe 16 is able to perform sample suction.

To facilitate understanding, in the following first embodiment, the first sampler unit 60 is simply referred to as a "rack sampler 60", and the second sampler unit 80 is simply referred to as a "disk sampler 80".

The rack sampler 60 includes a first belt 61 for movably holding a plurality of sample racks 18 in a horizontal direction (an arrow L1 direction), a second belt 62 connected to an edge portion of the first belt 61 in the L1 direction, a third belt 63 connected to the second belt 62 in the L1 direction, and a rack detector 64 for detecting sample racks 18 mounted on the first belt 61 and the second belt 62.

The rack sampler 60 further includes a first rack reader 65 for non-contact reading of a rack's ID of a sample rack 18 on the second belt 62 detected by the rack detector 64 and a first cuvette reader 66 for reading an identification data of a sample (sample's ID) written on a sample container 17.

The first belt 61 holds a plurality of sample racks 18 on waiting area A1. Each rack 18 holds sample containers 17 containing object samples classified as "general" so as to be closely spaced in a longitudinal direction of the belt. A sample rack 18 mounted on the waiting area A1 and detected by the rack detector 64 is moved in the rack moving L1 direction.

Since the first belt 61 can accommodate a plurality of closely arranged sample racks 18 along the rack moving L1 direction with no empty space, a large number of sample racks can be mounted.

On the interruption area A2 of the second belt 62, a sample rack 18 holding a sample container 17 containing object sample classified as "urgent" is mounted. The interruption area A2 includes an extracting position A3. At the extracting position A3, a sample rack holding a sample container that is required an urgent measurement is extracted in a direction to the disk sampler 80 (arrow L2 direction) by the first moving device 70. After extracting the "urgent" sample rack, the sample rack 18 moved by the first belt 61 and detected by the rack detector 64 is moved to the extracting position A3.

Since an "urgent" object sample needs to be measured in priority to a "general" object sample, when an "urgent" sample rack holding the "urgent" object sample container is placed on the interruption area A2, the first belt 61 stops its movement in the arrow L1 direction even though other sample racks are placed on the waiting area A1. After the "urgent" sample rack on the interruption area A2 is moved to the extracting position A3 and is extracted from the extracting position A3 by the first moving device 70, other sample racks on the waiting area A1 again start movements.

Accordingly, the "urgent" sample rack placed on the interruption area A2 can be quickly moved in the disk sampler 80.

The third belt 63 leaves the "urgent" sample rack to the leaving area A4 after completing suctions of the "general" object sample and the "urgent" object sample by the sample dispensing probe 16. Thus, the "urgent" sample rack extracted from the disk sampler 80 by the first moving device 70 in the arrow L3 direction is moved in the L1 direction.

The first rack reader 65 reads a rack's ID of the sample rack moved from the first belt 61 to the second belt 62. The first rack reader 65 further reads the rack ID of a sample rack placed on the interruption area A2 and detected by the rack detector 64. The first cuvette reader 66 reads a sample ID of a sample container 17 held by a sample rack 18, the rack ID of which is read by the first rack reader 65 and which is moving from the extracting position A3 in an L2 direction by the first moving device 70.

The first moving device 70 is provided from a downside of the rack sampler 60 to a downside of the disk sampler 80 for bringing in the sample rack 18 held by the second belt 62 in the rack sampler 60 at the extracting position A3 from the rack sampler 60 to the disk sampler 80 through the first lane 71. Further, the first moving device 70 ejects the sample rack 18 moved to the disk sampler 80 through the second lane 72 neighboring the first lane 71 onto the third belt 63 of the rack sampler 60.

It is also possible to modify the construction so as that a sample rack 18 can be brought in from the rack sampler 60 to the disk sampler 80 and be ejected vice versa through a common lane.

The disk sampler 80 includes a disk 81, a second rack reader 82 and a second cuvette reader 83. The disk 81 rotatably holds a smaller number of sample racks than the racks on the first belt 61 of the rack sampler 60 so as to rotate in an arrow R direction. The second rack reader 82 non-contact reads a rack's ID of the sample rack 18 rotated by the disk 81. The second cuvette reader 83 reads a sample's ID of a sample container 17 held by the sample rack 18 of which rack's ID is read by the second rack reader 82.

The disk sampler 80 further includes a fluid level detector 84 and a sampler cover 85. The fluid level detector 84 includes, for instance, a sensor such as an ultrasound type displacement sensor for detecting a fluid level of a sample in a sample container 17 whose sample's ID was read by the cuvette reader 83. The sampler cover 85 detachably covers the disk 81, the sample rack 18 supported by the disk 81, the second rack reader 82, the second cuvette reader 83 and the fluid level detector 84.

The circular disk 81 supports one or more "standard" sample racks 18s and "control" sample racks 18c on a preliminarily designated area (not shown) in a radial fashion from a center opening of the disk. On the other hand, one or more "general" patient sample racks 18G and "urgent" patient sample racks 18U transferred from the rack sampler 60 into the disk sampler 80 through the first moving device 70 are radially arranged in an area other than the preliminarily designated area. In connection with a rotation of the disk, each sample rack has an ID which is read by the second rack reader 82. Then, the second moving device 90 moves and stops a target sample rack at an extracting position B1 (a horizontal direction of the disk 85 in FIG. 5).

The "standard" sample racks 18S and "control" sample racks 18c placed on the designated area need not be moved into the rack sampler 60 through the first moving device 70 but are held on the disk 81 until an operator of the automatic analysis apparatus 100 bring out it from the designated area.

Namely, the "control" sample rack 18C can be rotated on the disk 81 disk 81 until when an operator brought out it from the disk sampler 80. Accordingly, it becomes possible to repeatedly stop the "control" sample rack 18C at the extracting position B1. As a result, the second moving device 90 can repeatedly move a particular "control" sample to a suctioning position through the sample dispensing probe 16.

The second container reader 83 reads each sample ID of sample containers held on the sample rack placed on the extracting position B1 and moved by the second moving device 90 in a rack moving L1 direction and an opposite rack moving L4 direction.

The sampler cover 85 includes a through-hole 851. The sample dispensing probe 16 rotates along a rotation track T and goes through the through-hole 851 into the sample rack that is moved from the extracting position B1 by the second moving device 90 for suctioning a sample contained in a sample container held by the rack. The sampler cover 85 is provided for ensuring safety of an operator against the moving disk 81 and the movement of the second moving device 90. The disk 81 moves the "control" sample 18C downward of the through-hole 851 at an instructed interval supplied from the operation unit 50.

Accordingly, if the sampler cover 85 is removed from the analysis unit 24 during a measurement, both the disk sampler unit 5 and the sample dispensing probe 16 stop their operations. When the sampler cover 85 is again fitted on the analysis unit 24, the disk 81 begins to rotate, and the second rack reader 82 reads the rack ID of the sample rack on the rotating disk 81 for recognizing all sample racks held by the disk 81.

It is, of course, possible to provide an interruption area on the disk 81 for preferentially performing a dispensing of an "urgent" object sample. Namely, the sampler cover 85 is taken off and an "urgent" sample rack 18u holding the "urgent" object sample is placed on the interruption area to move a suction position through the dispensing probe. Further, it is possible to construct the second sampler unit 80 so that an urgent sample container containing an urgent target sample or an urgent target sample rack holding the urgent sample container can be directly placed on a movable position provided in the second sampler unit 80.

Figure 6:
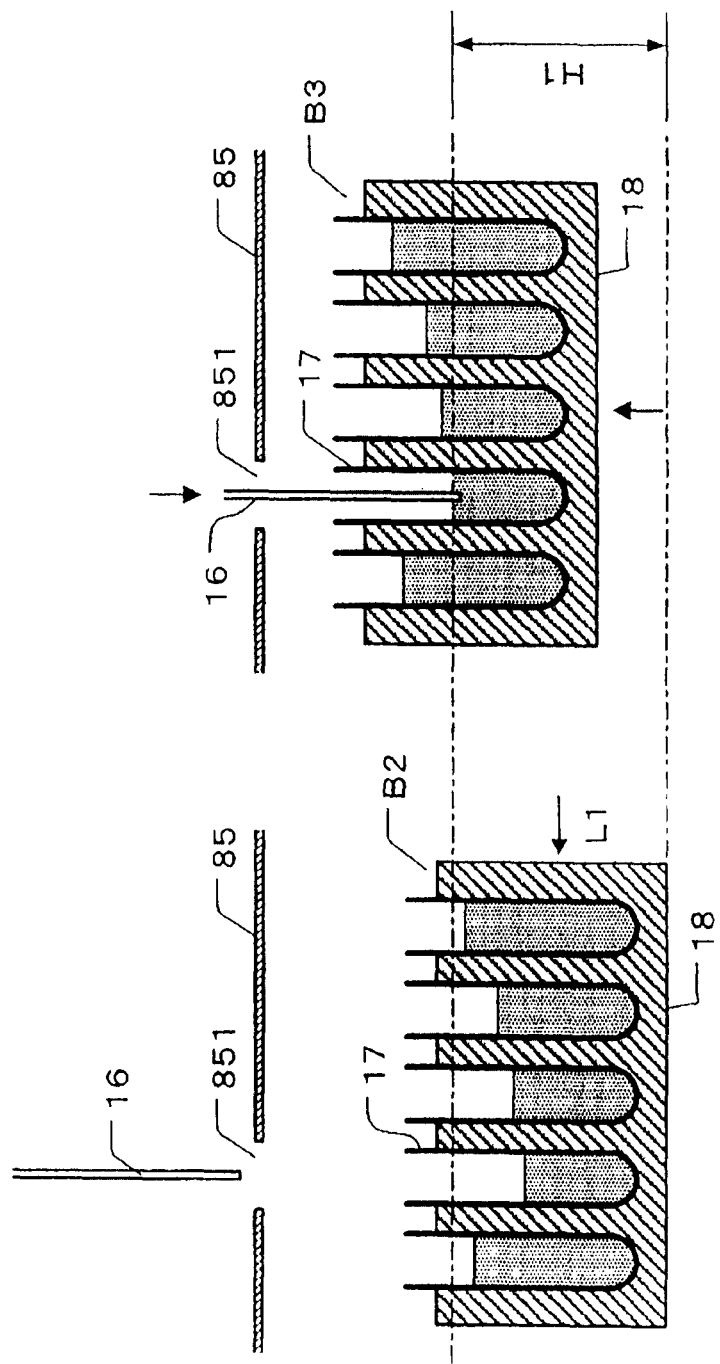
FIGS. 6A and 6B are sectional illustrations of movements of the sample rack so that a sample dispensing probe can suction a sample at a single position.

The second moving device 90 is provided on the disk sampler 80 and includes a third moving device 91 and a fourth moving device 92. The third moving device 91 moves the sample rack placed at the extracting position B1 in the rack moving direction L1 and the opposite moving direction L4. The fourth moving device 92 moves the sample rack moved by the third moving device 91 to the up-and-down directions (FIG. 6).

When a target sample rack 18T has its rack ID read by the second rack reader 82 and is stopped at the extracting position B1, as illustrated in FIG. 6A, the target sample rack 18T is moved in the horizontal L1 direction by the third moving device 91. When a fluid level of a target sample container 17T is detected by the fluid level detector 84, the target sample container 17T is stopped at the first suction position B2 positioned directly beneath the sampler cover through-hole 851. When the sample dispense through the sample dispensing probe 16 is finished, the target sample container 17T is stopped at the first suction position B2, the sample rack 18 moves in a rack moving L4 direction opposite to the L1 direction and stops at the extracting position B1.

As just described, the sample racks placed on the waiting area A1 and the interruption area A2 of the rack sampler 60 and the sample racks 18 placed on the designated area of the disk sampler 80 can be moved to the first suction position B2.

As shown in FIG. 6B, the fourth moving device 92 moves the sample rack stopped at the first suction position B2 in upper direction. A fluid level of a measuring sample container 17 mounted on the moved sample rack is detected by the fluid level detector 84, and it is stopped at a second suction position B3 that is a height H1 from the upper surface of the disk 81.

The sample dispensing probe 16 moves downward through the sampler cover through-hole 851 for suctioning the measuring sample stopped at the detected position by the sample sensor 16a.

It is also possible to provide a through-hole at a bottom portion of the sample rack so as to connect each of opening sections, and to provide an arm driving device so as to move the arm upward and downward so as to move the measuring sample container held by the sample rack that is stopped at the first suction position B2 in the upward direction. The measuring sample container is stopped at the second suction position B3 where a fluid level of the measuring sample has a height H1 from the upper surface from the disk. Further, it is possible to provide a free-space that operates as an urgent rack introduction entrance in the first sampler unit for placing an urgent target sample container containing an urgent target sample or an urgent target sample rack holding the urgent target sample container.

By moving the sample racks placed on both of the waiting area A1 and the interruption area A2 in the sampler 60 and the sample racks placed on the designated area of the disk sampler 80 relative to the second suction position B3, it becomes possible to fix the suctioning position of the sample dispensing probe 16 at the second suction position B3 only so as that the sample dispensing probe 16 moves in a horizontal direction and moves upward and downward at the fixed position. Consequently, it is possible resolve a small difference of ejection amounts that occurs when the samples suctioned at different positions are ejected into a reaction cuvette. Accordingly, a small sample dispensing accuracy can be improved.

Figure 7:
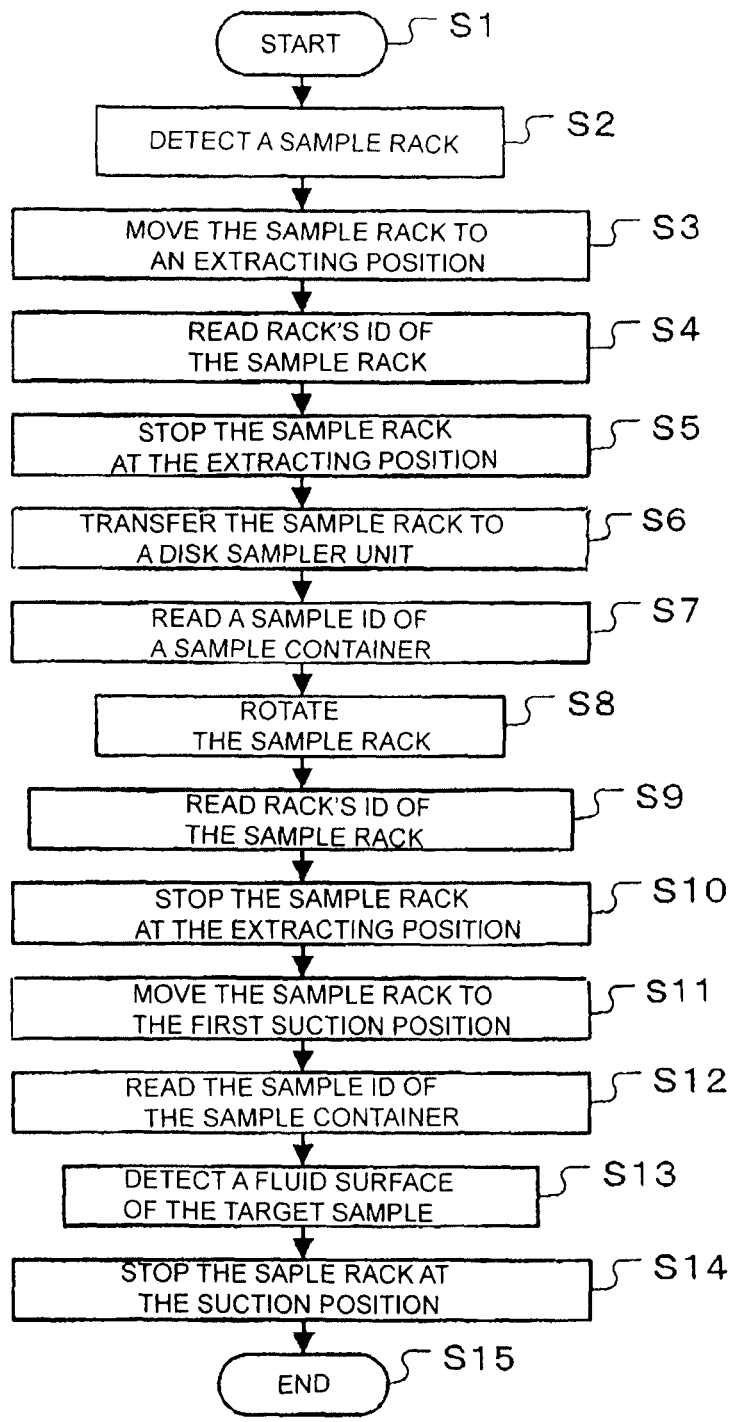
FIG. 7 is a flowchart illustrating an operation of the automatic analysis apparatus consistent with the embodiment.

FIG. 7 is a flowchart illustrating operations of the automatic analysis apparatus consistent with the present embodiment. The memory circuit in the system control unit 51 stores analysis parameters of each analyzing item set by an analysis parameter setting and the sample ID of an object sample set by an object sample data setting screen in the display unit 42 (FIG. 1) and analyzing item data.

For instance, when a sample rack holding one sample container containing a "general" object sample is placed at the waiting area in the rack sampler and a measurement start is instructed by the operation unit, the automatic analysis apparatus 100 starts the operation (step S1).

As shown in FIG. 1, the analysis unit 24 starts the operation based on the instruction of the system control unit 51. The first rack detector 64 of the rack sampler 60 detects a sample rack placed at the waiting area A1 (step S2).

The first belt 61 moves the sample rack detected by the rack detector 64 in a rack moving L1 direction. The second belt 62 moves the sample rack moved by the first belt 61 in the L1 direction at the extracting position A3 (step S3).

The first rack reader 65 reads the rack ID of the sample rack 18 that is moved in the L1 direction to the extracting position A3 by the second belt 62 (step S4). The second belt 62 stops the sample rack 18 whose rack ID is read by the first rack reader 65 at the extracting position A3 (step S5).

The first moving device 70 transfers the stopped sample rack 18 at the extracting position A3 in a rack introduction direction (L2 direction) of the disk sampler 80 (step S6). The first container reader 66 reads a sample ID of the sample container 17 held by the sample rack 18 that is moving in a rack introduction L2 direction from the extracting position A3 by the first moving device 70 (step S 7).

The first moving device 70 moves the sample rack holding the sample container whose sample ID is read by the first container reader 66 on the disk 81 of the disk sampler 80. The disk 81 rotates the sample rack moved by the first moving device 70 in a disk rotation R direction (step S8).

The second rack reader reads a rack's ID of the sample rack 18 rotated by the disk 81 (step S9). The disk 81 rotates the sample rack whose rack ID is read by the first rack reader 65 and the second rack reader 82 and stops it at the extracting position B1 (step S10).

The third moving device 91 in the second moving device 90 moves the stopped sample rack at the extracting position B1 in a rack moving L1 direction to the first suction position B2 (step S11). The second container reader 83 reads the sample ID of the sample container held by the sample rack that is moving from the extracting position B1 to the rack moving L1 direction by the third moving device 91 (step S12).

The fluid level detector 84 detects a fluid level of an object sample in the sample container whose sample ID is read by the first container reader 66 and the second container reader 83 (step S13).

The fourth moving device 92 moves the stopped sample rack at the first suction position B2 upward and stops it at second suction position B3 where a fluid level in the sample container is detected by the fluid level detector 84 as a height H1 from the upper surface of the disk 81 (step S14).

The sample dispensing probe 16 moves downward trough through-hole 851 in the sampler cover 85 and enters into a sample container 17 located directly beneath the through-hole 851. When a sample sensor 16a detects a second suction position B3 at a predetermined height H at which a lower end portion of the sample dispensing probe 16 touches to a target sample in a container, the sample dispensing probe 16 stops moving and starts suctioning. After finishing the suction, the sample dispensing probe 16 rotates onto a reaction cuvette and ejects the suctioned sample into the reaction cuvette at an ejecting position.

After completing the sample dispensing, the fourth moving device 92 moves the sample rack positioned at the second suction position B3 downward and stops it at the same height to the disk surface. Then, the third moving device 91 moves the stopped sample rack in a rack moving L4 direction and stops it at the extracting position B1.

The disk 81 rotates the sample rack stopped at the extracting position B1 and stops it at the extracting position B4. The first moving device 70 moves the sample rack 18 at the extracting position B4 and stops it on the third belt 63. The third belt 63 moves the sample rack 18 in the rack moving L1 direction.

When the object sample ejected in the reaction cuvette 3 is measured and the output unit 40 outputs analysis data resulting the measurement, the system control unit 51 supplies a measuring stop instruction and the automatic analysis apparatus 100 finishes the operation (step S15).

It is also possible to increase the dispensing accuracy of the first reagent by another embodiment. For example, an up-and-down device can be provided to move a reagent container stopped at a suction possible position through a dispense probe so as to detect a fluid level fluid level in the first reagent container. Then, the reagent container stopped at the suction position moves upward and stops so as that the detected fluid level reaches at the predetermined height for suctioning the first reagent in the reagent container through the first reagent dispense probe.

According to the first embodiment, it becomes possible to transfer a sample rack placed on a waiting area or an interruption area in a rack sampler that can repeatedly dispense the "control" sample through the sample dispensing probe to a disk sampler and can mount a larger number of sample racks than the disk sampler through a first moving device.

Further, it becomes possible to suction a plurality of samples at a single dispensing position by moving a sample rack placed on a designated area in the disk and by rotating the sample rack moved by a first moving device to an extracting position to a sample suction position by a second moving device.

In the described embodiment, the third moving device can be move the sample rack stopped at the extracting position to the first suction position for the sample dispensing probe. Further it can move the sample rack stopped at the first suction position to the second suction position by the fourth moving device 92. Thus, the sample dispensing probe can suction the sample at the second suction position.

As a result, the suctioning position of the sample dispensing probe in a horizontal direction can be fixed at the first suction position and maintained as a single position. Consequently, dispensing accuracy of a sample can be increased without losing the respective conveniences of the rack sampler and the disk sampler. Further, since the sample suctioning position through the dispensing probe in a horizontal direction and an up-and-down direction is fixed at only the second suctioning position, the dispensing accuracy of the sample can be much increased without losing convenience.

Figure 8:
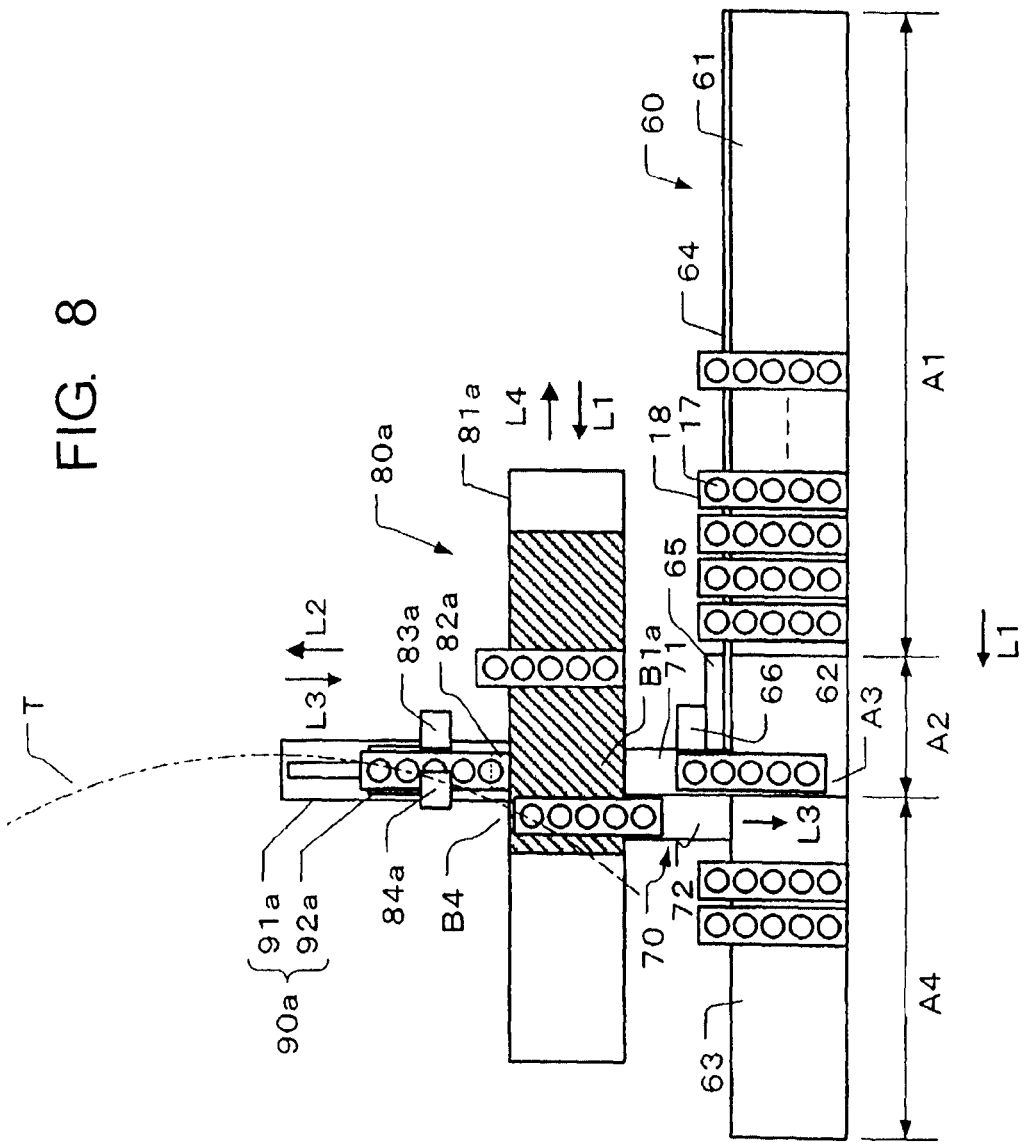
FIG. 8 is a schematic block diagram of another embodiment of the sampler unit and the moving device in the automatic analysis apparatus shown in FIG. 1.

FIG. 8 illustrates another embodiment in which a rack sampler 80a replaces the disk sampler 80 shown as the second sampler unit in the first embodiment, a second moving device 90a replaces the second moving device 90 shown in the first embodiment.

The rack sampler 80a as the second sampler unit includes a fourth belt 81a, a rack reader 82a, a container reader 83a and a fluid level detector 84a. The fourth belt 81a movably holds a smaller number of sample racks 18 than the sample racks held on the first belt 61 shown in the rack sampler 60 as the first sampler unit in the L1 and L4 directions.

The rack reader 82a is non-contacting and reads a rack ID of a sample rack 18 moved from the rack sampler 60 as the first sampler unit onto the fourth belt 81a by the first moving device 70 by. The container reader 83a reads a sample ID of the sample container 17 held by the sample rack 18 of which rack's ID has read by the rack reader 82a. The fluid level detector 84a detects a fluid level of the sample container 17 whose sample ID has read the container reader 83a.

The fourth belt 81a arranges "general" sample racks 18G and "control" sample racks 18C at a preliminarily designated area. Further, the fourth belt 81a holds "general" sample racks 18G and one or more "urgent" sample rack 18U, moved from the first rack sampler 60 by the first moving device 70.

The sample racks are moved in the L1 direction or the L4 direction, and each rack ID is read by the rack reader 82a. Then, the sample rack stops at stops at an extracting position B1a by the second moving device 90a. The sample racks placed on the designated area are not moved to the rack sampler 60 by the first moving device 70 but are held on the fourth belt 81a until an operator of the automatic analysis apparatus brings them out from the designated area.

The container reader 83a reads a sample ID of the sample container 17 held on the sample rack that is moving from the extracting position B1a by the second moving device 90a among the plurality of sample racks that are held on the fourth belt 81a after reading each rack ID through the rack reader 82a.

The second moving device 90a includes the third moving device 91a and the fourth moving device 92a. The third moving device 91a moves a sample rack held on the fourth belt 81a of the rack sampler 80a at the extracting position B1a in the L2 direction and the L3 direction. The fourth moving device 92a moves sample rack 18 transferred by the third moving device 91a in up-and-down directions.

The third moving device 91a moves the sample rack 18 whose rack ID has been read by the rack reader 82a in the rack sampler 80*a* and stopped at the extracting position B1*a* in the L2 direction for stopping at the first suctioning position. At the first suctioning position, the sample dispensing probe 16 can be moved downward into a target sample container which is held by the sample rack and of which fluid level is detected by the fluid level detector 84*a* in the second sampler unit 80*a*. The third moving device 91*a* further moves sample rack 18 that stops at the first suction position B2*a* after finishing sample dispense through the sample dispensing probe 16 in the L4 direction and stops at the extracting position B1*a*.

The fourth moving device 92*a* moves the sample rack stopped at the first suctioning position B2*a* in an upward direction. Then the fourth moving device 92*a* stops it at a second suctioning position at which a fluid level of a target sample contained in the sample container 17 detected by the fluid level detector 84*a* reaches a height H from upper surface of the fourth belt 81*a*.

By providing the second rack sampler 80*a* that can repeatedly dispense the control sample through the sample dispensing probe 16 and the first rack sampler 60 that can contain a larger number of sample racks 18 than the second rack sampler 80*a*, it becomes possible to move the sample racks placed in the waiting area A1 and the interruption area A2 of the first rack sampler 60 onto the fourth belt 81*a* in the second rack sampler 80*a* by the first moving device 70.

Further, the sample rack placed on the designated area on the fourth belt 81*a* and the sample rack moved by the first moving device 70 are moved to the extracting position B1*a* by the fourth belt 81*a*. And it is possible to move the sample rack moved to the extracting position B1*a* to a suctioning position for the sample dispensing probe 16

The sample rack 18 stopped at the extracting position B1*a* can be moved to the first suction position by the third moving device 91*a*. The sample rack stopped at the first suction position can be moved to the second suction position by the fourth moving device 92*a*.

As just described, the suctioning position through the sample dispensing probe 16 in a horizontal direction is fixed to the first suction position and maintained as a single position. Accordingly, the sample dispensing accuracy can be improved without losing convenience. Since the suction position of the sample dispensing probe 16 in a horizontal direction and up-and-down directions are fixed at the fixed second suction position (as a single position), the sample dispensing accuracy can be improved.

These embodiments are considered as exemplary only, and other embodiments consistent with the present invention will be apparent to those skilled in the art from consideration of the specification and practice of the present invention disclosed herein. For instance, while the sample rack has transferred from the rack sampler to the disk sampler in the first embodiment, of course, it is possible to construct so that the sample rack can be transferred from the disk sampler to the rack sampler for suctioning the sample at a single sample dispensing position.

Further, it is possible to place both of the sample dispensing position for the rack sampler and the sample dispensing position for the disk sampler at the common single sample dispensing position. Thus, it is possible to transfer each of the sample racks delivered from the rack sampler and the disk sampler to the common sample dispensing position for performing suctioning of the sample by the sample dispensing probe.

It is intended that the specification and examples be considered as exemplary only, with a true scope and spirit of the present invention being indicated by the following claims.

The invention claimed:

1. An automatic analysis apparatus comprising:
    a first sampler unit configured to movably mount in parallel a plurality of regular first sample racks, each holding a plurality of sample containers, the first sampler unit including a waiting area for mounting a plurality of regular sample racks, an interruption area for mounting an urgent regular sample rack and a leaving area;
    a second sampler unit configured to mount at least one control sample rack in a preliminarily designated area and radially arrange the plurality of regular sample racks in areas other than the preliminarily designated area;
    a first moving device configured to transfer a target sample rack among the plurality of regular sample racks mounted on the waiting area or the interruption area of the first sampler unit onto the areas other than the preliminarily designated area of the second sampler unit and to eject the regular sample rack from the second sampler unit;
    a second moving device provided under the second sampler unit and configured to transfer each of the plurality of regular sample racks radially mounted on the second sampler unit to an extracting position of the second sampler unit;
    wherein the second moving device includes a third moving device configured to move the target sample rack placed at the extracting position of the second sampler unit in a horizontal rack moving direction to a fixed sample dispensing position and a fourth moving device configured to move the target sample rack moved by the third moving device in up-and-down directions at the fixed sample dispensing position; and
    a sample dispensing probe configured to suction each sample contained in each of the transferred sample containers mounted on the target sample rack at the fixed sample dispensing position.

2. The automatic analysis apparatus according to claim 1 further including a fluid level detector configured to detect a fluid level of a sample contained in each of the plurality of second sample containers held on a plurality of target sample racks moved outside of the second sampler unit by the second moving device.

3. The automatic analysis apparatus according to claim 1, wherein the third moving device is configured to stop the target sample rack at a suctioning position of a predetermined height when a fluid level of the target sample is detected by the fluid level detector.

4. The automatic analysis apparatus according to claim 1, wherein the first moving device is configured to transfer the target sample rack mounted on the first sampler unit to the second sampler unit through a first lane, and to transfer the target sample rack moved in the second sampler unit to the first sampler unit through a second lane.

5. The automatic analysis apparatus according to claim 1, wherein the first moving device is configured to transfer the target sample rack mounted on the first sampler unit to the second sampler unit through a common lane, and to transfer the target sample rack moved in the second sampler unit to the first sampler unit through the common lane.

6. The automatic analysis apparatus according to claim 1, wherein the first sampler unit comprises a first belt configured to move the plurality of sample racks placed on a waiting area of the first belt in one direction; and a second belt connected at one edge portion of the first belt so as to successively move the target sample rack along the one direction;
    wherein the second belt includes an extracting position provided in an interruption area of the second belt;

whereby the first belt is configured to stop movement of the plurality of sample racks when the target sample rack is placed on the interruption area of the second belt, and to restart movement of the plurality of sample racks when the target sample rack is transferred to the second sampler unit through the extracting position by the first moving device.

7. The automatic analysis apparatus according to claim 1, wherein the first sampler unit includes a free-space that operates as an urgent rack introduction entrance, wherein the free-space can be used to place an urgent target sample container containing an urgent target sample or an urgent target sample rack holding the urgent target sample container.

8. The automatic analysis apparatus according to claim 1, wherein the second sampler unit is constructed so as that an urgent target sample container containing an urgent target sample or an urgent target sample rack holding the urgent target sample container can be directly provided in the second sampler unit.

9. An automatic analysis apparatus comprising:
- a rack sampler unit configured to movably mount a plurality of first sample racks, each holding a plurality of sample containers;
- a disk sampler unit configured to movably mount a plurality of second sample racks different from the plurality of first sample racks mounted on the first sampler unit;
- a first moving device configured to draw a target sample rack among the plurality of first sample racks mounted on the rack sampler unit into the disk sampler unit;
- a second moving device configured to set each of a plurality of target containers mounted on the target sampler rack drawn into the disk sampler unit at a fixed sample dispensing position by moving the target sample rack along in an upper direction from a surface of the disk sampler unit, the second moving device including a third moving device configured to move the target sample rack placed at an extracting position of the disk sampler unit in a horizontal rack moving direction to a fixed sample dispensing position and a fourth moving device configured to move the target sample rack moved by the third moving device in up-and-down directions at the fixed sample dispensing position; and
- a sample dispensing probe configured to suction each sample contained in each of the target containers at the fixed sample dispensing position.

10. The automatic analysis apparatus according to claim 9, wherein the second moving device moves the target sample rack in a vertical direction in order to set each of the plurality of target containers mounted on the target sample rack at the fixed sample dispensing position.

11. The automatic analysis apparatus according to claim 9 further including
- a first container reader configured to read each identification data of the plurality sample containers held by the rack sampler unit;
- a second container reader configured to read each identification data of the plurality of sample containers held on the target sample rack drawn into the disk sampler unit;
- whereby the target sample container can be directly set into the disk sampler unit during a period when the sample dispensing probe is stopping a dispensing operation.

12. The automatic analysis apparatus according to claim 9 wherein the rack sampler unit includes a free-space that operates as an urgent introduction entrance, wherein the free-space can be used to place an urgent target sample container containing an urgent sample or an urgent target sample rack holding the urgent target sample container.

* * * * *